United States Patent
Kitajima et al.

(10) Patent No.: US 9,079,827 B2
(45) Date of Patent: Jul. 14, 2015

(54) PROCESS FOR PRODUCTION OF AROMATIC AMIDE CARBOXYLIC ACID DERIVATIVE

(75) Inventors: Kazuki Kitajima, Mobara (JP); Kenji Kodaka, Oamishirasato (JP); Hiroyuki Katsuta, Chiba (JP); Kunio Okumura, Mobara (JP)

(73) Assignee: Mitsui Chemicals Agro, Inc., Tokyo (JP)

( * ) Notice: Subject to any disclaimer, the term of this patent is extended or adjusted under 35 U.S.C. 154(b) by 0 days.

(21) Appl. No.: 13/981,254

(22) PCT Filed: Jan. 23, 2012

(86) PCT No.: PCT/JP2012/051353
§ 371 (c)(1),
(2), (4) Date: Jul. 23, 2013

(87) PCT Pub. No.: WO2012/102239
PCT Pub. Date: Aug. 2, 2012

(65) Prior Publication Data
US 2013/0317247 A1    Nov. 28, 2013

(30) Foreign Application Priority Data
Jan. 25, 2011    (JP) .................... 2011-013410

(51) Int. Cl.
| | |
|---|---|
| C07C 233/81 | (2006.01) |
| C07C 233/88 | (2006.01) |
| C07C 231/02 | (2006.01) |
| C07C 231/12 | (2006.01) |
| C07C 233/66 | (2006.01) |
| C07C 253/30 | (2006.01) |
| C07C 255/60 | (2006.01) |

(52) U.S. Cl.
CPC ............. *C07C 231/12* (2013.01); *C07C 233/66* (2013.01); *C07C 253/30* (2013.01); *C07C 255/60* (2013.01)

(58) Field of Classification Search
USPC ........................................................ 564/184
See application file for complete search history.

(56) References Cited

U.S. PATENT DOCUMENTS

| | | | |
|---|---|---|---|
| 3,988,358 | A | 10/1976 | Heck |
| 2007/0293547 | A1 | 12/2007 | Molteni et al. |
| 2010/0160303 | A1 | 6/2010 | Liu et al. |

FOREIGN PATENT DOCUMENTS

| | | |
|---|---|---|
| EP | 0034292 | 8/1981 |
| JP | 56-125346 | 10/1981 |
| JP | 8-104661 | 4/1996 |
| JP | 2003-48859 | 2/2003 |
| JP | 2005-220107 | 8/2005 |
| JP | 2007-523087 | 8/2007 |
| TW | 201028401 | 8/2010 |
| WO | 2010/018857 | 2/2010 |
| WO | 2010/080481 | 7/2010 |

OTHER PUBLICATIONS

Konig et al. Chem. Ber., 103, 788 (1970).*
Russian Office Action dated Sep. 29, 2014 issued in the corresponding Russian patent application No. 2013138523/04(058285); English translation thereof.
Japanese Office Action dated Jun. 24, 2014, Application No. 2012-554785; English Translation included.
Taiwanese Office Action dated Nov. 25, 2014 issued in the corresponding Taiwanese patent application No. 101102890 ; English translation thereof.
Yasuhiro Torisawa et al. "Beneficial Effect of Cesium Salts on Pd-Catalyzed Hydroxycarbonylation" Bioorganic & Medicinal Chemistry Letters, Elsevier Science Ltd., 2000, vol. 10, pp. 2493-2495, Table 2.
Andrew S. Felts et al. "3-Cyano-5-fluoro-N-arylbenzamides as negative allosteric modulators of mGlu5: Identification of easily prepared tool compounds with CNS exposure in rats" Bioorganic & Medicinal Chemistry Letters, Jun. 15, 2010 (Available online), vol. 20, pp. 4390-4394, p. 4392, Table 4.
Yehoshua Ben-David et al. "Chelate-Assisted, Pd-Catalyzed Efficient Carbonylation of Aryl Chlorides" American Chemical Society, 1989, vol. 111, pp. 8742-8744.
International Search Report dated Feb. 28, 2012 filed in PCT/JP2012/051353.

* cited by examiner

*Primary Examiner* — Nyeemah A Grazier
(74) *Attorney, Agent, or Firm* — Rankin, Hill & Clark LLP

(57) ABSTRACT

The invention provides a method for producing an aromatic amide carboxylic acid derivative represented by the following Formula (2), including a step of reacting an aromatic amide halide derivative represented by the following Formula (1) with carbon monoxide. In the following Formulae (1) and (2), $R^1$ represents a hydrogen atom or an alkyl group having 1 to 6 carbon atoms; $X^1$ represents a fluorine atom or a cyano group; $X^2$ represents a halogen atom; and n represents an integer of from 0 to 3.

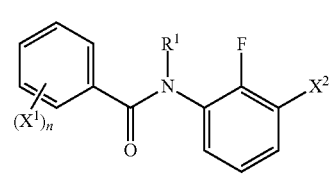

(1)

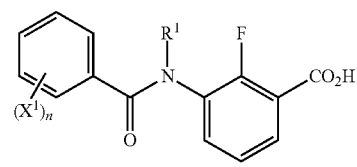

(2)

3 Claims, No Drawings

PROCESS FOR PRODUCTION OF AROMATIC AMIDE CARBOXYLIC ACID DERIVATIVE

TECHNICAL FIELD

The invention relates to a method for producing an aromatic amide carboxylic acid derivative.

BACKGROUND ART

Methods for producing aromatic carboxylic acid derivatives are known in which carbon monoxide is inserted into a certain kind of aromatic halide derivative in the presence of a base and water, using a palladium compound as a catalyst (see, for example, Japanese Patent Application Laid-Open (JP-A) Nos. 8-104661, 2003-48859, and 2005-220107).

Furthermore, a method for producing an aromatic amide carboxylic acid derivative having an amide bond and a halogen atom, etc., in the molecule thereof is known (see, for example, International Patent Publication No. WO 2010/18857).

SUMMARY OF INVENTION

Technical Problem

The inventors have studied industrial methods for producing aromatic amide carboxylic acid derivatives using the methods described in the above known art. However, the methods require multi-step reactions and are therefore insufficient as industrial production methods.

The invention provides a method that allows for the production of an aromatic amide carboxylic acid derivative having a halogen atom, etc., through fewer process steps, and a useful intermediate for use in the production method.

Solution to Problem

As a result of the intensive studies to develop a method that allows for the production of an aromatic amide carboxylic acid derivative having a halogen atom, etc., through fewer process steps, and is applicable for industrial production, the inventors have found a novel production method which can solve the above-mentioned problems and have achieved the invention. Furthermore, the inventors have found a useful intermediate for use in the method for producing an aromatic amide carboxylic acid derivative according to the invention and have achieved the invention.

That is, the invention includes the following aspects.

<1> A method for producing an aromatic amide carboxylic acid derivative represented by the following Formula (2), including a step of reacting an aromatic amide halide derivative represented by the following Formula (1) with carbon monoxide.

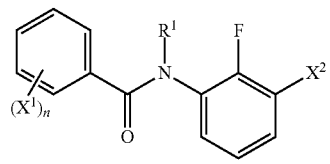

(1)

In Formula (1), $R^1$ represents a hydrogen atom or an alkyl group having 1 to 6 carbon atoms; $X^1$ represents a fluorine atom or a cyano group; and $X^2$ represents a halogen atom. n represents an integer of from 0 to 3.

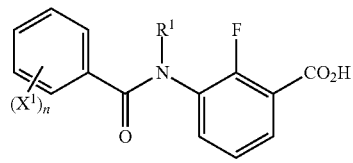

(2)

In Formula (2), $R^1$, $X^1$, and n have the same definitions as $R^1$, $X^1$, and n in Formula (1), respectively.

<2> The method for producing an aromatic amide carboxylic acid derivative according to <1>, further including a step of alkylating an aromatic amide halide derivative represented by the following Formula (3) when $R^1$ in Formula (1) represents an alkyl group having 1 to 6 carbon atoms.

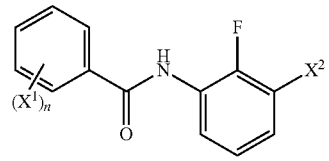

(3)

In Formula (3), $X^1$, $X^2$, and n have the same definitions as $X^1$, $X^2$, and n in Formula (1), respectively.

<3> The method for producing an aromatic amide carboxylic acid derivative according to <1>, further including a step of reacting an aniline derivative represented by the following Formula (4) with an aromatic carboxylic acid derivative represented by the following Formula (5) to obtain the aromatic amide halide derivative represented by Formula (1).

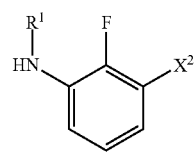

(4)

In Formula (4), $R^1$ and $X^2$ have the same definitions as $R^1$ and $X^2$ in Formula (1), respectively.

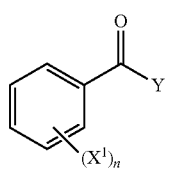

(5)

In Formula (5), $X^1$ and n have the same definitions as $X^1$ and n in Formula (1), respectively. Y represents a fluorine atom, a chlorine atom, or a bromine atom.

<4> An aromatic amide halide derivative represented by the following Formula (1).

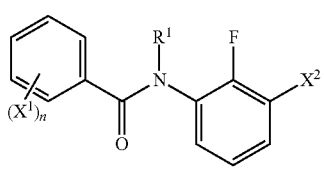

(1)

In Formula (1), $R^1$ represents a hydrogen atom or an alkyl group having 1 to 6 carbon atoms; $X^1$ represents a fluorine atom or a cyano group; $X^2$ represents a halogen atom; and n represents an integer of from 0 to 3.

<5> The aromatic amide halide derivative according to <4>, wherein, in Formula (1), $R^1$ represents a methyl group, $X^1$ represents a fluorine atom, $X^2$ represents a chlorine atom, and n represents 0 or 1.

Advantageous Effects of Invention

According to the invention, there can be provided a method that allows for the production of an aromatic amide carboxylic acid derivative having a halogen atom, etc., through fewer process steps, and a useful intermediate for use in the production method.

DESCRIPTION OF EMBODIMENTS

As used herein, the term "step" indicates not only a separate step but also a step that is not clearly distinguished from other steps as long as the desired effect of the step is obtained therefrom. As used herein, the notation "to" expressing a numerical range indicates a range including the numerical values before and after "to", as the minimum value and the maximum value, respectively.

In the definition of the general formulae, the following terms used herein have the meanings as explained below.

The term "halogen atom" indicates a fluorine atom, a chlorine atom, a bromine atom, or an iodine atom, "n-" means normal, "i-" means iso, "s-" means secondary, and "t-" means tertiary.

The term "alkyl group having 1 to 6 carbon atoms" refers to a linear or branched alkyl group having 1 to 6 carbon atoms, such as a methyl group, an ethyl group, an n-propyl group, an i-propyl group, an n-butyl group, an i-butyl group, an s-butyl group, a t-butyl group, an n-pentyl group, an i-pentyl group, a neopentyl group, a 4-methyl-2-pentyl group, an n-hexyl group or a 3-methyl-n-pentyl group.

In Formula (1) and Formula (2), each of the "alkyl group having 1 to 6 carbon atoms" represented by $R^1$ may have a substituent. The substituent may be one or more substituents selected from the group consisting of an unsubstituted linear or branched alkyl group having 1 to 6 carbon atoms, an unsubstituted cyclic cycloalkyl group having 3 to 8 carbon atoms, an unsubstituted linear, branched or cyclic alkenyl group having 2 to 6 carbon atoms, an unsubstituted linear, branched or cyclic alkynyl group having 2 to 6 carbon atoms, a halogen atom, a phenyl group, an amino group, a cyano group, a hydroxy group, an alkyloxy group, a benzyloxy group, an alkylthio group, a carboxy group, a benzyl group, a heterocyclic group, a phenylsulfonyl group, a phenylcarbonyl group and a phenylamino group.

When the alkyl group having 1 to 6 carbon atoms represented by $R^1$ has two or more substituents, the substituents may be the same as or different from one another. These substituents may each have an additional substituent where possible, and specific examples of the additional substituent include the substituents described above.

Specific examples of the "alkyl group having 1 to 6 carbon atoms" having a substituent include a methoxymethyl group, a benzyloxymethyl group, a phenacyl group, a p-bromophenacyl group, a p-methoxyphenacyl group, a trichloroethyl group, a 2-chloroethyl group, a 2-methylthioethyl group, a 1-methyl-1-phenylethyl group, a cinnamyl group, a benzyl group, a 2,4,6-trimethylbenzyl group, an o-nitrobenzyl group, a p-nitrobenzyl group, a p-methoxybenzyl group, and a 4-picolyl group.

The compounds represented by Formula (1) and Formula (2) according to the invention may each contain one or more asymmetric carbon atoms or asymmetric centers in their structures, and may therefore exist as two or more optical isomers. Embodiments of the invention encompass all of the optical isomers of the corresponding compounds and mixtures containing these optical isomers in any proportions.

The compounds represented by Formula (1) and Formula (2) according to the invention may each contain two or more geometrical isomers derived from a carbon-carbon double bond in their structures. Embodiments of the invention encompass all of the mixtures containing geometrical isomers of the corresponding compounds in any proportions.

Hereinbelow, the method for producing the aromatic amide carboxylic acid derivative according to the invention, and the compound that can be used as a production intermediate preferably used in the method and the method for producing the compound are described, but the invention is not limited thereto.

The method for producing the aromatic amide carboxylic acid derivative represented by the following Formula (2) according to the invention includes a carboxylation step in which the aromatic amide halide derivative represented by the following Formula (1) is reacted with carbon monoxide. The production method may include an additional step as necessary.

The carboxylation step allows for the production of the desired aromatic amide carboxylic acid derivative through fewer process steps. Furthermore, this production method is applicable for industrial production.

The carboxylation step of the production method is not specifically limited as long as the aromatic amide halide derivative represented by Formula (1) can react with carbon monoxide. In terms of the reaction yield, the carboxylation step is preferably a step in which the reaction is conducted in the presence of palladium or at least one palladium compound, and at least one phosphine compound and water, and more preferably a step in which the reaction is conducted in the presence of palladium or at least one palladium compound, and at least one phosphine compound, at least one inorganic salt and water.

The aromatic amide carboxylic acid derivative represented by Formula (2) produced by the production method according to the invention is suitably used as an intermediate for producing amide derivatives having prominent pest-control effects, such as those described in International Patent Publication Nos. WO2010/013567 and WO2010/018714.

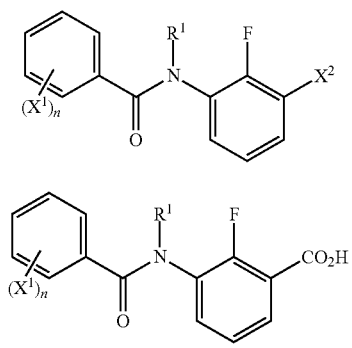

In Formula (1) and Formula (2), $R^1$ represents an alkyl group having 1 to 6 carbon atoms; $X^1$ represents a fluorine atom or a cyano group; $X^2$ represents a halogen atom; and n, which represents the number of the substituent(s) $X^1$, is an integer of from 0 to 3.

In the carboxylation step of the production method, palladium or at least one palladium compound is preferably used.

Examples of the form of palladium or the palladium compound used include inorganic acids, organic acids, supported palladium and colloidal metals. Any form of palladium or palladium compound can be used without any restrictions.

Specific examples of palladium or the palladium compound include palladium (II) chloride, palladium (II) bromide, palladium (II) iodide, palladium (II) acetate, palladium (II) nitrate, palladium (II) propionate, bis(triphenylphosphine) palladium (II) chloride, bis(triphenylphosphine) palladium (II) bromide, bis(benzonitrile) palladium (II) chloride, bis(triphenylphosphine) palladium (II) acetate, tetrakis (triphenylphosphine) palladium (0), metal palladium, palladium carbon, palladium alumina, palladium silica, palladium-barium carbonate, palladium black and colloidal palladium. Among these, palladium acetate (II), palladium chloride (II) and palladium carbon are preferable.

In a case in which palladium or the palladium compound is used in the carboxylation step, the amount of palladium or the palladium compound used is not particularly limited, and generally from 0.01% by mol to 10% by mol, preferably from 0.03% by mol to 2% by mol, with respect to the amount of the aromatic amide halide derivative represented by Formula (1).

In the carboxylation step of the production method according to the invention, at least one phosphine compound is preferably used. For example, the phosphine compound functions as a ligand of palladium or a palladium compound, thereby improving the yield of the resulting aromatic amide carboxylic acid derivative.

Examples of the phosphine compound include triisopropylphosphine, tributylphosphine, triphenylphosphine, tris(4-methylphenyl)phosphine, tris(3-methylphenyl)phosphine, tris(2-methylphenyl)phosphine, tris(2-dimethylaminophenyl)phosphine, dimethylphenylphosphine, 1,1-bis(dimethylphosphino)methane, 1,2-bis(diethylphosphino)methane, 1,2-bis(dimethylphosphino)ethane, 1,2-bis(diethylphosphino)ethane, 1,3-bis(dimethylphosphino)propane, 1,4-bis(dimethylphosphino)butane, 1,1-bis(diphenylphosphino)methane, 1,2-bis(diphenylphosphino)ethane, 1,3-bis(diphenylphosphino)propane, 1,4-bis(diphenylphosphino)butane and 1,5-bis(diphenylphosphino)pentane. Among these, 1,3-bis(diphenylphosphino)propane and 1,4-bis(diphenylphosphino)butane are preferable.

In the production method, each of palladium, the palladium compound and the phosphine compound may be used singly, or a complex of palladium and the phosphine compound or a complex of the palladium compound and the phosphine compound prepared in advance may be used.

In a case in which palladium or the palladium compound is used singly, the amount of the phosphine compound added is not specifically limited. For example, the amount of the phosphine compound added may be 1 or more equivalents, generally 2 to 100 equivalents, with respect to 1 equivalent of palladium or the palladium compound. It is preferable that 4 to 50 equivalents of the phosphine compound are used.

It is preferable to use at least one inorganic base in the carboxylation step of the production method as necessary. It is more preferable to use at least one inorganic base selected from the group consisting of phosphates, acetates, formates and carbonates.

Examples of the inorganic base include phosphates such as dipotassium monohydrogen phosphate, potassium dihydrogen phosphate, tripotassium phosphate, disodium monohydrogen phosphate, sodium dihydrogen phosphate, trisodium phosphate, diammonium monohydrogen phosphate, ammonium dihydrogen phosphate and triammonium phosphate; acetates such as potassium acetate, sodium acetate and ammonium acetate; formates such as potassium formate and sodium formate; carbonates such as potassium carbonate, sodium carbonate, potassium hydrogen carbonate and sodium hydrogen carbonate; and alkali metal hydroxides such as lithium hydroxide, sodium hydroxide and potassium hydroxide. These inorganic bases may be used singly, or in combination of two or more kinds thereof.

In a case in which the inorganic base is used in the carboxylation step, the amount of the inorganic base used is not specifically limited. The inorganic base may be used in a molar amount of from 0.1 to 100 times the molar amount of the aromatic amide halide derivative represented by Formula (1). The inorganic base is preferably used in a molar amount of from 1 to 10 times the molar amount of to the aromatic amide halide derivative represented by Formula (1).

In the carboxylation step, it is preferable to use at least one inorganic base selected from the group consisting of phosphates, acetates, formates and carbonates in a molar amount of from 0.1 to 100 times the molar amount of the aromatic amide halide derivative represented by Formula (1), and it is more preferable to use at least one inorganic base selected from the group consisting of phosphates, acetates and carbonates in a molar amount of from 1 to 10 times the molar amount of the aromatic amide halide derivative represented by Formula (1).

In the carboxylation step, a base other than the inorganic base may be used with the inorganic base as necessary. Examples of the base other than the inorganic base include organic bases such as triethylamine, tri-n-propylamine, tri-n-butylamine, piperidine, pyridine, 2-picoline, 3-picoline, 2,6-lutidine, N-methylmorpholine, N-ethylmorpholine, N,N-diethylaniline, N-ethyl-N-methylaniline, diisopropylethylamine, 3-methylimidazole, 1,8-diazabicyclo[5.4.0]-7-undecene, 1,4-diazabicyclo[2.2.2]octane and 4-dimethylaminopyridine; and metal alcoholates such as sodium methoxide and sodium ethoxide.

In a case in which the base other than the inorganic base is used, the base is used in a molar amount of from 0.1 to 100 time, preferably from 1 to 10 times the molar amount of the aromatic halide derivative represented by Formula (1).

In general, carbon monoxide used in the carboxylation step of the production method may be any carbon monoxide as long as it can be used for organic synthesis reactions. The carboxylation step is conducted at normal pressure or under increased pressure. For example, the carbon monoxide pressure may be appropriately selected within the range of from 0.1 MPa to 30 MPa. The carbon monoxide pressure is preferably from 0.2 MPa to 20 MPa.

The amount of carbon monoxide used in the carboxylation step is not specifically limited. For example, the molar ratio of carbon monoxide to the aromatic amide halide derivative represented by Formula (1) is from 0.1 to 50, and preferably from 1.0 to 20.0.

Any method of charging a reactor vessel with carbon monoxide may be used as long as the method is safe and the reaction is not inhibited thereby. Examples thereof include a method in which all of the carbon monoxide is added at one time at the start of the reaction, a method in which the carbon monoxide is added in several batches during the reaction, and a method in which the carbon monoxide is added while keeping the pressure fixed.

The carboxylation step is preferably conducted in the presence of water. The water to be used may be any water as long as the reaction is not affected thereby.

In a case in which water is used, the amount of water used is not specifically limited. Water is generally used in a mass amount of from 0.1 to 10 times, preferably from 0.1 to 2 times the mass amount of the aromatic amide halide derivative represented by Formula (1).

The carboxylation step may be conducted in the presence of an organic solvent and water. Any organic solvent may be used as long as the reaction is not significantly inhibited thereby. Examples of the organic solvent include alkylated aromatic hydrocarbon solvents such as benzene, toluene and xylene; substituted aromatic hydrocarbon solvents such as cyanobenzene and nitrobenzene; aliphatic hydrocarbon solvents such as n-heptane, n-tetradecane and cyclohexane; halogenated aliphatic hydrocarbon solvents such as dichloromethane, chloroform and carbon tetrachloride; nitriles such as acetonitrile and propionitrile; alcohol solvents such as methanol, ethanol, isopropyl alcohol, 1-decanol and benzyl alcohol; linear and cyclic ether solvents such as diethyl ether, dioxane, tetrahydrofuran, 1,2-dimethoxyethane and t-butyl methyl ether; ester solvents such as ethyl acetate and butyl acetate; ketone solvents such as acetone, cyclohexanone, butanone and methyl isobutyl ketone; and polar aprotic solvents such as N,N-dimethylformamide, N,N-dimethylacetamide, N-methylpyrrolidone, dimethylsulfoxide, sulfolane and 1,3-dimethyl-2-imidazolidinone.

In terms of the product yield, it is preferable to use at least one solvent selected from the group consisting of alkylated aromatic hydrocarbon solvents, acyclic or cyclic ether solvents and polar aprotic solvents, and it is more preferable to use at least one solvent selected from the group consisting of alkylated aromatic hydrocarbon solvents.

These organic solvents may be used singly, or in combination of or two or more kinds thereof.

In a case in which the organic solvent is used, the amount of the organic solvent used is not specifically limited. The organic solvent is generally used in a mass amount of from 1 to 10 times the mass amount of the aromatic amide halide derivative represented by Formula (1).

Furthermore, in a case in which the organic solvent is used, the ratio of the amount of water to the amount of the organic solvent is preferably from 10% by mass to 80% by mass, more preferably from 10% by mass to 70% by mass.

It is preferable that the carboxylation step is conducted using, as a solvent, water and at least one organic solvent, with the ratio of the amount of water being from 10% by mass to 80% by mass relative to the amount of the organic solvent. It is more preferable that the carboxylation step is conducted using water and at least one alkylated aromatic hydrocarbon as the organic solvent, with the ratio of the amount of water being from 10% by mass 70% by mass relative to the amount of the organic solvent.

The reaction temperature of the carboxylation step may be appropriately selected including room temperature under the reaction pressure. The carboxylation step can be generally conducted at a temperature of from 50° C. to 250° C., preferably at a temperature of from 100° C. to 200° C.

The reaction time may be appropriately selected depending on the scale of the reaction, the reaction temperature or the like. The reaction time may be appropriately selected within the range of from several minutes to 96 hours, preferably from 1 hour to 24 hours.

Following the completion of the carboxylation step, another carboxylation step may be conducted by separating the resultant aromatic amide carboxylic acid from the organic solvent layer, and adding another aromatic amide halide derivative represented by Formula (1) and inorganic salt to the remaining organic solvent layer.

After the completion of the reaction, the aromatic amide carboxylic acid derivative represented by Formula (2) thus obtained may be isolated from the reaction mixture by a common separation and purification method such as extraction, concentration, neutralization, filtration, recrystallization, column chromatography or distillation. Furthermore, the target compound can be used for the next step without isolating it from the reaction system.

When $R^1$ in Formula (1) represents the alkyl group having 1 to 6 carbon atoms, the method for producing the aromatic amide carboxylic acid derivative represented by Formula (2) according to the invention preferably includes an alkylation step in which an aromatic amide halide derivative represented by the following Formula (3) is alkylated to obtain an aromatic amide halide derivative represented by Formula (1).

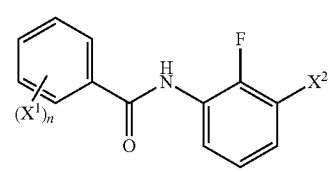

(3)

In Formula (3), $X^1$ represents a fluorine atom or a cyano group; $X^2$ represents a halogen atom; and n represents an integer of from 0 to 3.

As a method for alkylating the aromatic amide halide derivative represented by Formula (3) to obtain the aromatic amide halide derivative represented by Formula (1), any method usually used for alkylating an amido group may be used without any restrictions.

For example, the aromatic amide halide derivative represented by Formula (3) may be reacted with a predetermined reactant in a solvent using a base to produce the aromatic amide halide derivative represented by Formula (1) in which $R^1$ is an alkyl group.

As the solvent, any organic solvent may be used as long as the alkylation reaction is not inhibited thereby. Examples thereof include aromatic hydrocarbon solvents such as benzene, toluene, xylene and chlorobenzene; halogenated aliphatic hydrocarbon solvents such as dichloromethane, chloroform and carbon tetrachloride; nitriles such as acetonitrile and propionitrile; linear and cyclic ether solvents such as diethyl ether, dioxane, tetrahydrofuran, 1,2-dimethoxyethane and t-butyl methyl ether; ester solvents such as ethyl acetate and butyl acetate; ketone solvents such as acetone, cyclohexanone, butanone and methyl isobutyl ketone; alcohol solvents such as methanol and ethanol; polar aprotic solvents such as N,N-dimethylformamide, N,N-dimethylacetamide, N-methylpyrrolidone, dimethylsulfoxide, sulfolane and 1,3-dimethyl-2-imidazolidinone; and water. These solvents may be used singly, or in combination of or two or more kinds thereof. The amount of the solvent used is not specifically limited, and the solvent is generally used in a mass amount of from 1 to 10 times the mass amount of the aromatic amide halide derivative represented by Formula (3).

Examples of the base include organic bases such as triethylamine, tri-n-butylamine, pyridine and 4-dimethylaminopyridine; alkali metal hydroxides such as lithium hydroxide, sodium hydroxide and potassium hydroxide; carbonates such as sodium hydrogen carbonate, potassium hydrogen carbonate, sodium carbonate and potassium carbonate; phosphates such as trisodium phosphate, tripotassium phosphate, triammonium phosphate, disodium monohydrogen phosphate, dipotassium monohydrogen phosphate and diammonium monohydrogen phosphate; acetates such as sodium acetate, potassium acetate and ammonium acetate; metal alcoholates such as sodium methoxide and sodium ethoxide; and alkali metal hydrides such as sodium hydride. The base is used in an molar amount of from 0.01 to 100 times, preferably from 0.1 to 5 times the molar amount of the aromatic amide halide derivative represented by Formula (3).

As the reactant, an alkylating agent may be used. Examples thereof include alkyl halide compounds such as methyl iodide, ethyl bromide, ethyl iodide, n-propyl iodide and 2,2,2-trifluoroethyl iodide; and alkyl sulfates such as dimethyl sulfate and diethyl sulfate.

The amount of the reactant used may be appropriately selected within the range of from 1 molar equivalent to 5 molar equivalents, with respect to the amount of the aromatic amide halide derivative represented by Formula (3). The reactant may be also used as a solvent.

The reaction temperature and the reaction time are not specifically restricted. For example, the reaction temperature may be from −80° C. to the reflux temperature of the solvent used. The reaction time may be from several minutes to 96 hours. Each of the reaction temperature and the reaction time can be appropriately selected.

It is preferable that the method for producing the aromatic amide carboxylic acid derivative represented by Formula (2) further includes an amidation step, in which an aniline derivative represented by the following Formula (4) is reacted with an aromatic carboxylic acid derivative represented by the following Formula (5) to obtain the aromatic amide halide derivative represented by Formula (3).

(4)

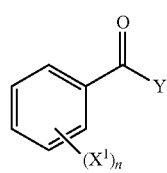

(5)

In Formula (4) and Formula (5), $X^1$ represents a fluorine atom or a cyano group, $X^2$ represents a halogen atom, $R^1$ represents a hydrogen atom or an alkyl group having 1 to 6 carbon atoms; n represents an integer of from 0 to 3; and Y represents a fluorine atom, a chlorine atom, or a bromine atom.

The aromatic amide halide derivative represented by Formula (3) may be produced by the amidation reaction of the aniline derivative represented by Formula (4) with the aromatic carboxylic acid derivative represented by Formula (5) in an appropriate solvent or in the absence of solvent. In the amidation step, an appropriate base or solvent can be used.

Any solvent may be used in the amidation step as long as the reaction is not significantly inhibited thereby. Examples thereof include alkylated aromatic hydrocarbon solvents such as benzene, toluene and xylene; halogenated aromatic hydrocarbon solvents such as chlorobenzene and dichlorobenzene; substituted aromatic hydrocarbon solvents such as cyanobenzene and nitrobenzene; aliphatic hydrocarbon solvents such as n-heptane, n-tetradecane and cyclohexane; halogenated aliphatic hydrocarbon solvents such as dichloromethane, chloroform and carbon tetrachloride; substituted aliphatic hydrocarbon solvents such as nitromethane; linear and cyclic ether solvents such as diethyl ether, dioxane, tetrahydrofuran, 1,2-dimethoxyethane and t-butyl methyl ether; ester solvents such as ethyl acetate and butyl acetate; ketone solvents such as acetone, cyclohexanone, butanone and methyl isobutyl ketone; nitrile solvents such as acetonitrile and propionitrile; polar aprotic solvents such as N,N-dimethylformamide, N,N-dimethylacetamide, N-methylpyrrolidone, dimethylsulfoxide, sulfolane and 1,3-dimethyl-2-imidazolidinone; and water. These solvents may be used singly, or in combination of two or more kinds thereof.

The amount of the solvent used is not specifically limited, and the solvent is generally used in a mass amount of from 1 to 10 times the mass amount of the aniline derivative represented by Formula (4).

Examples of the base used in the amidation step include organic bases such as triethylamine, tri-n-propylamine, tri-n-butylamine, piperidine, pyridine, 2-picoline, 3-picoline, 2,6-lutidine, N-methylmorpholine, N-ethylmorpholine, N,N-diethylaniline, N-ethyl-N-methylaniline, diisopropylethylamine, 3-methylimidazole, 1,8-diazabicyclo[5.4.0]-7-undecene, 1,4-diazabicyclo[2.2.2]octane and 4-dimethylaminopyridine; alkali metal hydroxides such as lithium hydroxide, sodium hydroxide and potassium hydroxide; carbonates such as sodium carbonate, potassium carbonate, sodium hydrogen carbonate and potassium hydrogen carbonate; phosphates such as dipotassium monohydrogen phosphate, potassium dihydrogen phosphate, trisodium phosphate, tripotassium phosphate, triammonium phosphate, disodium monohydrogen phosphate, sodium dihydrogen phosphate, diammonium monohydrogen phosphate and ammonium dihydrogen phosphate; acetates such as sodium acetate, potassium acetate and ammonium acetate; and metal alcoholates such as sodium methoxide and sodium ethoxide.

The base is used in an molar amount of from 0.01 to 100 times, preferably from 0.1 to 5 times the molar amount of the amount of the aromatic carboxylic acid derivative represented by Formula (5).

Alternatively, the aromatic amide halide derivative can be produced without using a base by removing acidic gas byproducts by passing an inert gas such as nitrogen or argon.

The reaction temperature and the reaction time in the amidation step are not specifically limited. For example, the reaction temperature may be from −20° C. to the reflux temperature of the solvent used. The reaction time may be from several minutes to 96 hours. Each of the reaction temperature and the reaction time can be appropriately selected.

The aromatic carboxylic acid derivative represented by Formula (5) can be readily produced from a corresponding aromatic carboxylic acid compound through an ordinary method using a halogenating agent. Examples of the halogenating agent include thionyl chloride, oxalyl chloride, phosgene, phosphorous oxychloride, phosphorus pentachloride, phosphorus trichloride, thionyl bromide, and phosphorus tribromide.

Alternatively, the aromatic amide halide derivative represented by Formula (3) may be produced by the reaction of an aromatic carboxylic acid compound corresponding to the aromatic carboxylic acid derivative represented by Formula (5) with the aniline derivative represented by Formula (4) in the absence of a halogenating agent.

Such method is described in, for example, Chem. Bet page 788 (1970).

Specific examples thereof includes a method using a carbodiimide condensing agent such as N,N'-dicyclohexylcarbodiimide or 1-ethyl-3-(3-dimethylaminopropyl)carbodiimide, with an additive such as 1-hydroxybenzotriazole or 1-hydroxysuccinimide as needed. A condensing agent other than the carbodiimide condensing agent may be used, and examples thereof include peptide condensing agents such as N,N-carbonyldi-1H-imidazole, diphenylphosphoryl azide and diethyl phosphorocyanidate. These condensing agents may be used singly.

The amount of the condensing agent used is not specifically limited. For example, the condensing agent may be used in a molar amount of from 1 to 5 times.

As the solvent, any inert solvent may be used as long as the reaction is not significantly inhibited thereby, and the inert solvent may be appropriately selected from the solvents described above.

The reaction temperature is generally from −50° C. to +100° C., preferably from −20° C. to +80° C.

An aniline derivative represented by Formula (4) in which $R^1$ is an alkyl group may be obtained by reacting, in a solvent, an aniline derivative represented by Formula (4) in which $R^1$ is a hydrogen atom with an aldehyde compound or a ketone compound, followed by a reaction under a hydrogen atmosphere in the presence of a catalyst.

Any solvent may be used as long as the reaction is not significantly inhibited thereby. Examples thereof include aromatic hydrocarbon solvents such as benzene, toluene, xylene and chlorobenzene; halogenated aliphatic hydrocarbon solvents such as dichloromethane, chloroform and 1,2-dichloroethane; nitrile solvents such as acetonitrile and propionitrile; linear and cyclic ether solvents such as diethyl ether, dioxane, tetrahydrofuran, 1,2-dimethoxyethane and t-butyl methyl ether; ester solvents such as ethyl acetate and butyl acetate; alcohol solvents such as methanol and ethanol; polar aprotic solvents such as N,N-dimethylformamide, N,N-dimethylacetamide, N-methylpyrrolidone, dimethylsulfoxide, sulfolane and 1,3-dimethyl-2-imidazolidinone; and water. These solvents may be used singly, or in combination of two or more kinds thereof.

Examples of the catalyst include palladium catalysts such as palladium carbon and palladium hydroxide carbon, nickel catalysts such as Raney nickel, cobalt catalysts, platinum catalysts, ruthenium catalysts, and rhodium catalysts.

The amount of the catalyst used is not specifically limited. For example, the catalyst may be used in a molar amount of from 0.05 to 0.5 times.

Examples of the aldehyde compound include formaldehyde, acetaldehyde, propionaldehyde, fluoroacetaldehyde, difluoroacetaldehyde, trifluoroacetaldehyde, chloroacetaldehyde, dichloroacetaldehyde, trichloroacetaldehyde, and bromoacetaldehyde.

The amount of the aldehyde compound used is not specifically limited. For example, the aldehyde compound may be used in a molar amount of from 1 to 3 times.

Examples of the ketone compound include acetone, butanone, and methyl isobutyl ketone.

The amount of the ketone compound used is not specifically limited. For example, the ketone compound may be used in a molar amount of from 1 to 3 times.

The reaction pressure may be appropriately selected within the range of from 1 atm to 100 atm. The reaction temperature may be appropriately selected within the range of from −20° C. to the reflux temperature of the solvent used, and the reaction time may be appropriately selected within the range of from several minutes to 96 hours.

Furthermore, an aniline derivative represented by Formula (4) in which $R^1$ is an alkyl group can be obtained by reacting, in a solvent, an aniline derivative represented by Formula (4) in which $R^1$ is a hydrogen atom with an aldehyde compound or a ketone compound, followed by treatment with a reducing agent.

As the solvent, any solvent may be used as long as the reaction is not significantly inhibited thereby. Examples thereof include aromatic hydrocarbon solvents such as benzene, toluene, xylene and chlorobenzene; halogenated aliphatic hydrocarbon solvents such as dichloromethane, chloroform and 1,2-dichloroethane; nitrile solvents such as acetonitrile and propionitrile; linear and cyclic ether solvents such as diethyl ether, dioxane, tetrahydrofuran, 1,2-dimethoxyethane and t-butyl methyl ether; ester solvents such as ethyl acetate and butyl acetate; alcohol solvents such as methanol and ethanol; polar aprotic solvents such as N,N-dimethylformamide, N,N-dimethylacetamide, N-methylpyrrolidone, dimethylsulfoxide, sulfolane and 1,3-dimethyl-2-imidazolidinone; and water. These solvents may be used singly, or in combination of two or more kinds thereof.

Examples of the aldehyde compound and the ketone compound include the same compounds as mentioned above.

Examples of the reducing agent include borohydrides such as sodium borohydride, sodium cyanoborohydride and sodium triacetate borohydride.

The amount of the reducing agent used is not specifically limited. For example, the reducing agent may be used in a molar amount of from 1 to 3 times.

The reaction temperature and the reaction time are not specifically limited. For example, the reaction temperature may be from −20° C. to the reflux temperature of the solvent used. The reaction time may be from several minutes to 96 hours. Each of the reaction temperature and the reaction time may be appropriately selected.

In addition, an aniline derivative represented by Formula (4) in which $R^1$ is an alkyl group can be obtained by reacting, in a solvent or in the absence of solvent, an aniline derivative represented by Formula (4) in which $R^1$ is a hydrogen atom with an aldehyde compound.

As the solvent, any solvent may be used as long as the reaction is not significantly inhibited thereby, and examples thereof include aromatic hydrocarbon solvents such as benzene, toluene, xylene and chlorobenzene; halogenated aliphatic hydrocarbon solvents such as dichloromethane, chloroform and 1,2-dichloroethane; nitrile solvents such as acetonitrile and propionitrile; linear and cyclic ether solvents such as diethyl ether, dioxane, tetrahydrofuran, 1,2-dimethoxyethane and t-butyl methyl ether; ester solvents such as ethyl acetate and butyl acetate; alcohol solvents such as methanol and ethanol; polar aprotic solvents such as N,N-dimethylformamide, N,N-dimethylacetamide, N-methylpyrrolidone, dimethylsulfoxide, sulfolane and 1,3-dimethyl-2-imidazolidinone; alcohol solvents such as methanol and ethanol; inorganic acids such as sulphuric acid and hydrochloric acid; organic acid solvents such as formic acid and acetic acid; and water. These solvents may be used singly, or in combination of two or more kinds thereof.

Examples of the aldehyde compound include formaldehyde, acetaldehyde, and propionaldehyde.

The amount of the aldehyde compound used is not specifically limited. For example, the aldehyde compound may be used in a molar amount of from 1 to 3 times.

The reaction temperature and the reaction time is not specifically limited. For example, the reaction temperature may be from −20° C. to the reflux temperature of the solvent used. The reaction time may be from several minutes to 96 hours. Each of the reaction temperature and the reaction time may be appropriately selected.

Amide derivatives having prominent pest-control effects can be efficiently produced by, for example, converting the aromatic amide carboxylic acid derivative represented by Formula (2) produced by the method for producing aromatic amide carboxylic acid derivatives according to the invention into an acid chloride and reacting it with a perfluoroalkylaniline derivative.

The aromatic amide halide derivative represented by Formula (1) according to the invention can be suitably used in the method for producing the aromatic amide carboxylic acid derivative represented by Formula (2). Therefore, the aromatic amide halide derivative represented by Formula (1) is a useful intermediate for the efficient production of the amide derivative having a prominent pest-control effect.

Representative examples of the aromatic amide halide derivatives represented by Formula (1) according to the invention are shown in Table 1 below, but the invention is not limited to these examples. In Table 1, "n-" represents normal, "i-" represents Iiso, "Me" represents a methyl group, "Et" represents an ethyl group, "n-Pr" represents a normal propyl group, "i-Pr" represents an isopropyl group, "n-Bu" represents a normal butyl group, "n-Pn" represents a normal pentyl group, "n-hex" represents a normal hexyl group, "CN" represents a nitrile group, "F" represents a fluorine atom, "Cl" represents a chlorine atom, "Br" represents a bromine atom, and "I" represents an iodine atom.

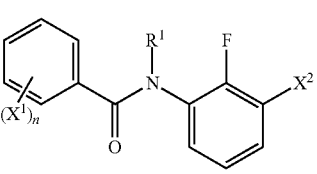

(1)

TABLE 1

| Compound | $X^1$ | | | | | | |
|---|---|---|---|---|---|---|---|
| Number | 2 | 3 | 4 | 5 | 6 | $R^1$ | $X^2$ |
| 1 | H | H | H | H | H | H | Cl |
| 2 | H | H | H | H | H | Me | Cl |
| 3 | H | H | H | H | H | H | Cl |
| 4 | H | H | H | H | H | Me | Cl |
| 5 | H | H | H | H | H | Et | Br |
| 6 | H | H | F | H | H | H | Cl |

TABLE 1-continued

| Compound | $X^1$ | | | | | | |
|---|---|---|---|---|---|---|---|
| Number | 2 | 3 | 4 | 5 | 6 | $R^1$ | $X^2$ |
| 7 | H | H | F | H | H | Me | Cl |
| 8 | H | H | F | H | H | H | Br |
| 9 | H | H | F | H | H | Et | Br |
| 10 | H | CN | H | H | H | n-Pr | I |
| 11 | H | CN | H | H | H | Me | Cl |
| 12 | H | CN | H | H | H | H | Cl |
| 13 | F | H | H | H | F | H | Cl |
| 14 | F | H | H | H | F | Me | Cl |
| 15 | H | H | CN | H | H | n-Bu | Cl |
| 16 | H | H | CN | H | H | n-Pn | Br |
| 17 | H | H | CN | H | H | n-Hex | I |

EXAMPLES

The present invention is explained below by reference to Examples, but the scope of the invention is not limited to these Examples. Chemical shifts for $^1$H-NMR are reported in ppm downfield from tetramethylsilane reference. In addition, "s" means singlet, "d" means doublet, "t" means triplet, "m" means multiplet, and "brs" means broad singlet. Unless otherwise specified, "%" means "percent by weight".

Example 1

Production of
N-(3-chloro-2-fluorophenyl)benzamide

Toluene (250 g) and water (150 g) were added to 50.0 g (0.34 mol) of 3-chloro-4-fluoroaniline and the mixture was heated to 60° C. Into this reaction mixture was added dropwise 50.7 g (0.36 mol) of benzoyl chloride. At the same time, a 10% aqueous sodium hydroxide solution was added dropwise thereto to maintain the pH around 8. After the dropwise addition was completed, the mixture was stirred for 2 hours and cooled in ice. The precipitate was filtered, washed with water, and dried to obtain 74.8 g of the title compound (yield: 87%) as a white solid.

$^1$H-NMR (CDCl$_3$, δppm) 7.11-7.18 (2H, m), 7.50-7.61 (3H, m), 7.88-7.90 (2H, m), 8.05 (1H, brs), 8.38-8.42 (1H, m).

Example 2

Production of
N-(3-chloro-2-fluorophenyl)-N-methylbenzamide

Into toluene (60 g) were added 85% potassium hydroxide (2.8 g, 0.05 mol) and 10.0 g (0.40 mol) of N-(3-chloro-2-fluorophenyl)benzamide obtained above. While the reaction mixture was heated at reflux, 6.1 g (0.05 mol) of dimethyl sulfate was added dropwise. The reaction was conducted with a dean stark trap to remove the water generated. After the dropwise addition was completed, the mixture was stirred for 1 hour and allowed to cool to room temperature. The resultant was mixed with 20 g of a 5% aqueous sodium hydroxide solution and stirred for 1 hour. The mixture was allowed to separate to give a toluene layer, which was washed with 40 g of water. The toluene layer was concentrated under reduced pressure, and the resultant residue was washed with n-hexane to obtain 9.97 g of the title compound (yield: 94%) as a white solid.

$^1$H-NMR (CDCl$_3$, δppm) 3.42(3H, s), 6.89-6.93 (2H, m), 7.19-7.33 (6H, m).

Example 3

Production of
2-fluoro-3-(N-methylbenzamide)benzoic acid

A stainless steel autoclave (100 mL) was charged with 1.98 g (0.0075 mol) of N-(3-chloro-2-fluorophenyl)-N-methylbenzamide obtained above, 1.91 g (0.009 mol) of tripotassium phosphate, 3.0 g of toluene, 2.0 g of water, 15.2 mg (0.0677 mmol) of palladium acetate, and 163 mg (0.395 mmol) of 1,3-bis(diphenylphosphino)propane. The autoclave was charged with carbon monoxide at 0.6 MPa and sealed, and the mixture was stirred at 180° C. for 3 hours. After being cooled to room temperature, the resultant was mixed with ethyl acetate and water and allowed to separate. The aqueous layer was acidified (to a pH of from 2 to 3) with dilute hydrochloric acid and extracted with ethyl acetate. The aqueous layer was then adjusted to a pH of from 5 to 6.5 with sodium hydrogen carbonate and extracted with ethyl acetate. The ethyl acetate layers were combined, washed with saturated brine, and dried over anhydrous magnesium sulfate. The magnesium sulfate was filtered off, and the filtrate was concentrated. The resultant residue was purified on silica gel column chromatography (eluent; n-hexane:ethyl acetate=1:2) to obtain 1.25 g of the title compound (yield: 61.0%) as a white solid.

$^1$H-NMR (CDCl$_3$, δppm) 3.45 (3H, s), 7.08 (1H, brs), 7.21-7.33 (5H, m), 7.85-7.88 (1H, brs).

The proton for the carboxylic acid was not observed.

Example 4

Production of
2-fluoro-3-(N-methylbenzamide)benzoic acid

A stainless steel autoclave (200 mL) was charged with 15.0 g (0.055 mol) of N-(3-chloro-2-fluorophenyl)-N-methylbenzamide obtained above, 16.19 g (0.165 mol) of potassium acetate, 9.36 g (0.0935 mol) of potassium hydrogen carbonate, 32.8 g of toluene, 3.95 g of water, 2.37 g of Pd/C (55.25% wet), and 0.949 g (0.0023 mol) of 1,3-bis(diphenylphosphino)propane. The autoclave was charged with carbon monoxide at 1.4 MPa and sealed, and the mixture was stirred at 180° C. for 7 hours. After being cooled to room temperature, the resultant was mixed with toluene, water, and a 20% aqueous KOH solution and allowed to separate. The aqueous layer was acidified to a pH of 1 with 6 N hydrochloric acid solution to precipitate a solid, which was filtered and dried to obtain 13.46 g of the title compound (yield: 90%) as a white solid.

Example 5

Production of 2-fluoro-3-benzamide benzoic acid

A stainless steel autoclave (100 mL) was charged with 1.87 g (0.0075 mol) of N-(3-chloro-2-fluorophenyl)benzamide obtained above, 1.91 g (0.009 mol) of tripotassium phosphate, 3.0 g of toluene, 2.0 g of water, 15.2 mg (0.0677 mmol) of palladium acetate, and 163 mg (0.395 mmol) of 1,3-bis(diphenylphosphino)propane. The autoclave was charged with carbon monoxide at 0.6 MPa and sealed, and the mixture was stirred at 180° C. for 3 hours. After being cooled to room temperature, the resultant was mixed with ethyl acetate and water and allowed to separate. The organic layer was washed with a 5% aqueous sodium hydroxide solution. The aqueous layer was acidified to a pH of 1 with concentrated hydrochloric acid to precipitate a solid, which was filtered and dried to obtain 0.93 g of the title compound (yield: 48%) as a light gray solid.

$^1$H-NMR (DMSO-d$_6$, δppm) 7.31 (1H, m), 7.55 (2H, m), 7.62 (1H, m), 7.72 (1H, m), 7.82 (1H, m), 7.99 (2H, m), 10.2 (1H, s).

Example 6

Production of
N-(3-chloro-2-fluorophenyl)-4-fluorobenzamide

In a manner similar to Example 1 using 50.0 g (0.34 mol) of 3-chloro-4-fluoroaniline, 57.0 g (0.36 mol) of p-fluorobenzyl chloride and 300 g of toluene, 82.9 g of the title compound (yield 90%) was obtained as a white solid.

$^1$H-NMR (CDCl$_3$, δppm) 7.13-7.22 (4H, m), 7.89-7.92 (3H, m), 8.35-8.38 (1H, m).

Example 7

Production of N-(3-chloro-2-fluorophenyl)-4-fluoro-
N-methylbenzamide

In a manner similar to Example 2 using 40.0 g (0.15 mol) of N-(3-chloro-2-fluorophenyl)-4-fluorobenzamide obtained above, 26.3 g (0.21 mol) of dimethyl sulfate, 13.4 g (0.24 mol) of 85% potassium hydroxide and 190 g of toluene, 35.9 g of the title compound (yield: 94.5%) was obtained as a white solid.

$^1$H-NMR (CDCl$_3$, δppm) 3.41 (3H, s), 6.88-6.91 (2H, s), 6.95-6.98 (2H, m), 7.24-7.28 (1H, m), 7.31-7.34 (2H, m).

Example 8

Production of
2-fluoro-3-(4-fluoro-N-methylbenzamide)benzoic
acid

A stainless steel autoclave (100 mL) was charged with 1.69 g (0.006 mol) of N-(3-chloro-2-fluorophenyl)-4-fluoro-N-methylbenzamide obtained above, 3.66 g (0.021 mol) of dipotassium monohydrogen phosphate, 3.60 g of toluene, 1.85 g of water, 12.2 mg (0.0543 mmol) of palladium acetate, and 130 mg (0.315 mmol) of 1,3-bis(diphenylphosphino) propane. The autoclave was charged with carbon monoxide at 0.6 MPa and sealed, and the mixture was stirred at 170° C. for 8 hours. After being cooled to room temperature, the resultant was mixed with ethyl acetate and water and allowed to separate. The aqueous layer was acidified (to a pH of from 2 to 3) with dilute hydrochloric acid and extracted with ethyl acetate. The aqueous layer was adjusted to a pH of from 5 to 6.5 with sodium hydrogen carbonate and extracted with ethyl acetate. The ethyl acetate layers were combined, washed with saturated brine, and dried over anhydrous magnesium sulfate. The magnesium sulfate was filtered off, and the filtrate was concentrated under reduced pressure. The resultant residue was purified on silica gel column chromatography (eluent; n-hexane:ethyl acetate=1:2) to obtain 1.55 g of the title compound (yield: 88.7%).

$^1$H-NMR (CDCl$_3$, δppm) 3.45 (3H, s), 6.88-6.91 (2H, brs), 7.11-7.14 (1H, m), 7.27-7.35 (3H, m), 7.88-7.91 (1H, m). The proton for the carboxylic acid was not observed.

Example 9

Production of
2-fluoro-3-(4-fluoro-N-methylbenzamide)benzoic
acid

A stainless steel autoclave (200 mL) was charged with 15.49 g (0.05 mol) of N-(3-chloro-2-fluorophenyl)-4-fluoro-N-methylbenzamide obtained above, 16.19 g (0.165 mol) of potassium acetate, 9.36 g (0.0935 mol) of potassium hydrogen carbonate, 32.8 g of toluene, 3.95 g of water, 2.37 g of Pd/C (55.25% wet), and 0.949 g (0.0023 mol) of 1,3-bis(diphenylphosphino)propane. The autoclave was charged with carbon monoxide at 1.4 MPa and sealed, and the mixture was stirred at 180° C. for 7 hours. After being cooled to room temperature, the resultant was mixed with toluene, water, and a 20% aqueous KOH solution and allowed to separate. The aqueous layer was acidified to a pH of 1 with 6 N hydrochloric acid to precipitate a solid, which was filtered and dried to obtain 13.46 g of the title compound (yield: 84%) as a white solid.

Example 10

Production of
2-fluoro-3-(4-fluorobenzamide)benzoic acid

A stainless steel autoclave (100 mL) was charged with 1.61 g (0.006 mol) of N-(3-chloro-2-fluorophenyl)-4-fluorobenzamide obtained above, 3.66 g (0.021 mol) of dipotassium monohydrogen phosphate, 3.60 g of toluene, 1.85 g of water, 12.2 mg (0.0543 mmol) of palladium acetate, and 130 mg (0.315 mmol) of 1,3-bis(diphenylphosphino)propane. The autoclave was charged with carbon monoxide at 0.6 MPa and sealed, and the mixture was stirred at 180° C. for 5.5 hours. After being cooled to room temperature, the resultant was mixed with ethyl acetate and water and allowed to separate. The organic layer was washed with a 5% aqueous sodium hydroxide solution. The aqueous layer was acidified to a pH of 1 with concentrated hydrochloric acid to precipitate a solid, which was filtered and dried to obtain 0.75 g of the title compound (yield: 45%) as a light gray solid.

$^1$H-NMR (DMSO-$d_6$, δppm) 8.07-7.38 (7H, m), 10.3 (1H, s), 13.3 (1H, s).

Example 11

Production of
N-(3-chloro-2-fluorophenyl)-3-fluorobenzamide

In a manner similar to Example 1 using 10.0 g (0.069 mol) of 3-chloro-4-fluoroaniline, 13.1 g (0.082 mol) of m-fluorobenzoyl chloride and 50 g of toluene, 16.9 g of the title compound (yield 92%) was obtained as a white solid.

$^1$H-NMR (CDCl$_3$, δppm) 7.12-7.20 (2H, m), 7.26-7.32 (1H, m), 7.49-7.53 (1H, m), 7.61-7.65 (2H, m), 8.01 (1H, s), 8.35-8.37 (1H, m).

Example 12

Production of N-(3-chloro-2-fluorophenyl)-3-fluoro-N-methylbenzamide

To 60 g of toluene were added 10.0 g (0.037 mol) of N-(3-chloro-2-fluorophenyl)-3-fluorobenzamide obtained above and 3.21 g (0.047 mol) of 85% potassium hydroxide. While the mixture was heated at reflux, 6.13 g (0.047 mol) of dimethyl sulfate was added dropwise. The reaction was conducted with a dean stark trap to remove the water generated. After the dropwise addition was completed, the mixture was stirred for 1.5 hours and allowed to cool to room temperature. The resultant was mixed with 30 g of a 5% aqueous sodium hydroxide solution, stirred for 1 hour, and allowed to separate. The toluene layer was concentrated under reduced pressure and the resultant residue was separated and purified on silica gel column chromatography using NH silica (eluent; n-hexane:ethyl acetate=4:1 to 2:1) to obtain 8.98 g of the title compound (yield: 85%) as a white solid.

$^1$H-NMR (CDCl$_3$, δppm) 3.42 (3H, s), 6.97-7.00 (3H, m), 7.00-7.08 (2H, m), 7.17-7.18 (1H, m), 7.25-7.28 (1H, m).

Example 13

Production of
N-(3-chloro-2-fluorophenyl-2,6-difluorobenzamide

In a manner similar to Example 1 using 10.0 g (0.069 mol) of 3-chloro-4-fluoroaniline, 14.5 g (0.082 mol) of m-fluorobenzoyl chloride and 50 g of toluene, 18.8 g of the title compound (yield: 96%) was obtained as a white solid.

$^1$H-NMR (CDCl$_3$, δppm) 7.02-7.06 (2H, m), 7.12-7.20 (2H, m), 7.44-7.50 (1H, m), 7.90 (1H, s), 8.34-8.43 (1H, m).

Example 14

Production of N-(3-chloro-2-fluorophenyl)-2,6-difluoro-N-methylbenzamide

To 60 g of toluene were added 10.0 g (0.039 mol) of N-(3-chloro-2-fluorophenyl)-2,6-difluorobenzamide obtained above and 3.22 g (0.050 mol) of 85% potassium hydroxide. While the mixture was heated at reflux, 6.34 g (0.050 mol) of dimethyl sulfate was added dropwise. The reaction was conducted with a dean stark trap to remove the water generated. After the dropwise addition was completed, the mixture was stirred for 2 hours and allowed to cool to room temperature. The resultant was mixed with 30 g of a 5% aqueous sodium hydroxide solution, stirred for 1 hour, and allowed to separate. The toluene layer was concentrated under reduced pressure and the resultant residue was purified on silica gel column chromatography using NH silica (eluent; n-hexane:ethyl acetate=4:1 to 1:1) to obtain 9.92 g of the title compound (yield: 86%) as a white solid.

$^1$H-NMR (CDCl$_3$, δppm) 3.42 (3H, s), 6.72-6.75 (2H, m), 6.90-6.94 (1H, m), 7.07-7.10 (1H, m), 7.16-7.25 (1H, m).

Example 15

Production of
2-fluoro-3-(2,6-difluoro-N-methylbenzamide)benzoic
acid

A stainless steel autoclave (100 mL) was charged with 1.80 g (0.006 mol) of N-(3-chloro-2-fluorophenyl)-2,6-difluoro-N-methylbenzamide obtained above, 3.66 g (0.021 mol) of dipotassium monohydrogen phosphate, 3.60 g of toluene, 1.85 g of water, 12.2 mg (0.0543 mmol) of palladium acetate, and 130 mg (0.315 mmol) of 1,3-bis(diphenylphosphino)propane. The autoclave was charged with carbon monoxide at 0.6 MPa and sealed, and the mixture was stirred at 180° C. for 5.5 hours. After being cooled to room temperature, the resultant was mixed with ethyl acetate and water and allowed to separate. The organic layer was washed with a 5% aqueous sodium hydroxide solution. The aqueous layer was acidified to a pH of 1 with concentrated hydrochloric acid to precipitate a solid, which was filtered and dried to obtain 1.57 g of the title compound (yield: 85%) as a white solid.

$^1$H-NMR (CDCl$_3$, δppm) 3.20 (3H, s), 6.99-7.00 (2H, m), 7.18-7.22 (1H, m), 7.32-7.38 (1H, m), 7.53-7.71 (1H, m), 7.72-7.74 (1H, m).

Example 16

Production of N-(3-chloro-2-fluorophenyl)-3-cyanobenzamide

In a manner similar to Example 1 using 7.0 g (0.048 mol) of 3-chloro-4-fluoroaniline, 9.55 g (0.058 mol) of m-cyanobenzoyl chloride and 35 g of toluene, 13.4 g of the title compound (quantitative yield) was obtained as a white solid. This compound was used in the next reaction without further purification.

$^1$H-NMR (CDCl$_3$, δppm) 7.14-7.18 (1H, m), 7.20-7.23 (1H, m), 7.66-7.69 (1H, m), 7.88-7.89 (1H, m), 8.01 (1H, s), 8.10-8.11 (1H, m), 8.20 (1H, s), 8.32-8.35 (1H, m).

Example 17

Production of N-(3-chloro-2-fluorophenyl)-3-cyano-N-methylbenzamide

To 60 g of toluene were added 7.0 g (0.026 mol) of N-(3-chloro-2-fluorophenyl)-3-cyanobenzamide obtained above and 2.19 g (0.033 mol) of 85% potassium hydroxide. While the mixture was heated at reflux, 4.19 g (0.033 mol) of dimethyl sulfate was added dropwise. The reaction was conducted with a dean stark trap to remove the water generated. After the dropwise addition was completed, the mixture was stirred for 2 hours and allowed to cool to room temperature. The resultant was mixed with 30 g of a 5% aqueous sodium hydroxide solution, stirred for 1 hour, and allowed to separate. The toluene layer was concentrated under reduced pressure and the resultant residue was purified on silica gel column chromatography using NH silica (eluent; n-hexane:ethyl acetate=3:1 to 2:1) to obtain 3.05 g of the title compound (yield: 44%) as a light pink oil.

$^1$H-NMR (CDCl$_3$, δppm) 3.44 (3H, s), 7.01-7.02 (2H, m), 7.28-7.31 (1H, m), 7.33-7.36 (1H, m), 7.52-7.53 (1H, m), 7.57-7.59 (1H, m), 7.63 (1H, s).

Example 18

Production of 2-fluoro-3-(3-cyano-N-methylbenzamide)benzoic acid

A stainless steel autoclave (100 mL) was charged with 1.65 g (0.006 mol) of N-(3-chloro-2-fluorophenyl)-3-cyano-N-methylbenzamide obtained above, 3.66 g (0.021 mol) of dipotassium monohydrogen phosphate, 3.60 g of toluene, 1.85 g of water, 12.2 mg (0.0543 mmol) of palladium acetate, and 130 mg (0.315 mmol) of 1,3-bis(diphenylphosphino)propane. The autoclave was charged with carbon monoxide at 0.6 MPa and sealed, and the mixture was stirred at 180° C. for 5 hours. After being cooled to room temperature, the mixture was mixed with ethyl acetate and water and allowed to separate. The organic layer was washed with a 5% aqueous sodium hydroxide solution. The aqueous layer was acidified to a pH of 1 with concentrated hydrochloric acid to precipitate a solid, which was filtered and dried to obtain 0.73 g of the title compound (yield: 41%) as a light green solid.

$^1$H-NMR (DMSO-d$_6$, δppm) 3.34 (3H, s), 7.13-7.99 (7H, m).

As illustrated above, the method for producing aromatic amide carboxylic acid derivatives according to the invention allows for the production of the desired aromatic amide carboxylic acid derivatives through fewer processes.

Japanese Patent Application No. 2011-013410 is herein incorporated by reference in its entirety.

All publications, patent applications, and technical standards mentioned in this specification are herein incorporated by reference to the same extent as if each individual publication, patent application, or technical standard was specifically and individually indicated to be incorporated by reference.

The invention claimed is:

1. A method for producing an aromatic amide carboxylic acid derivative represented by the following Formula (2), comprising a step of reacting an aromatic amide halide derivative represented by the following Formula (1) with carbon monoxide and water in the presence of: at least one selected from a group consisting of palladium and a palladium compound; at least one phosphine compound; and at least one selected from a group consisting of an inorganic base, an organic base and a metal alcoholate:

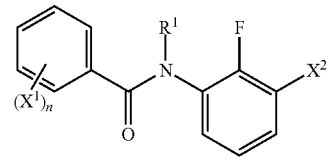

(1)

wherein, in Formula (1), R$^1$ represents a hydrogen atom or an alkyl group having 1 to 6 carbon atoms; X$^1$ represents a fluorine atom; X$^2$ represents a chlorine atom; and n represents 0 or 1,

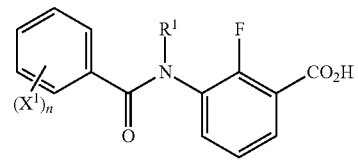

(2)

wherein, in Formula (2), R$^1$, X$^1$, and n have the same definitions as R$^1$, X$^1$, and n in Formula (1), respectively.

2. The method for producing an aromatic amide carboxylic acid derivative according to claim 1, further comprising a step of alkylating an aromatic amide halide compound represented by the following Formula (3) when R$^1$ in Formula (1) represents an alkyl group having 1 to 6 carbon atoms:

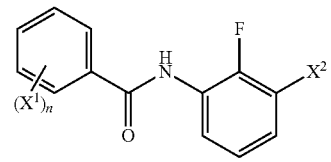

(3)

wherein, in Formula (3), X$^1$, X$^2$, and n have the same definitions as X$^1$, X$^2$, and n in Formula (1), respectively.

3. The method for producing an aromatic amide carboxylic acid derivative according to claim 1, further comprising a step of reacting an aniline derivative represented by the following Formula (4) with an aromatic carboxylic acid derivative represented by the following Formula (5) to obtain the aromatic amide halide derivative represented by Formula (1):

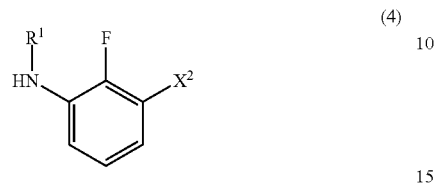

(4)

wherein, in Formula (4), $R^1$ and $X^2$ have the same definitions as $R^1$ and $X^2$ in Formula (1), respectively,

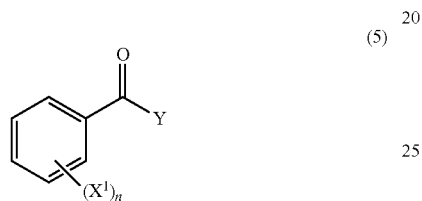

(5)

wherein, in Formula (5), $X^1$ and n have the same definitions as $X^1$ and n in Formula (1), respectively; and Y represents a fluorine atom, a chlorine atom or a bromine atom.

* * * * *